(12) United States Patent
Tischendorf et al.

(10) Patent No.: US 7,957,928 B2
(45) Date of Patent: Jun. 7, 2011

(54) METHOD FOR FUNCTION MONITORING OF A SENSOR

(75) Inventors: Axel Tischendorf, Leonberg (DE);
Hermann Straub, Rottenburg (DE);
Torsten Pechstein, Radebeul (DE)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 390 days.

(21) Appl. No.: 11/793,824

(22) PCT Filed: Nov. 29, 2005

(86) PCT No.: PCT/EP2005/056331
§ 371 (c)(1),
(2), (4) Date: Jan. 14, 2009

(87) PCT Pub. No.: WO2006/069879
PCT Pub. Date: Jul. 6, 2006

(65) Prior Publication Data
US 2009/0132194 A1    May 21, 2009

(30) Foreign Application Priority Data

Dec. 23, 2004 (DE) .......................... 10 2004 063 468

(51) Int. Cl.
*G01D 18/00* (2006.01)
(52) U.S. Cl. ...................... 702/104; 702/116; 707/104.1
(58) Field of Classification Search .................. 702/19, 702/85, 104, 116, 176; 600/345, 347, 365; 73/1.02; 707/104.1
See application file for complete search history.

(56) References Cited

U.S. PATENT DOCUMENTS

| | | | |
|---|---|---|---|
| 6,856,930 B2 * | 2/2005 | Ammann | 702/116 |
| 7,366,626 B2 * | 4/2008 | Hazama et al. | 702/104 |
| 2004/0139110 A1 * | 7/2004 | LaMarca et al. | 707/104.1 |

FOREIGN PATENT DOCUMENTS

| | | |
|---|---|---|
| DE | 101 00 239 A1 | 7/2002 |
| DE | 101 41 408 A1 | 3/2003 |
| DE | 102 09 318 A1 | 9/2003 |
| EP | 1 550 861 A1 | 7/2005 |
| JP | 05209858 | 8/1993 |
| JP | 11-51757 | 2/1999 |
| JP | 2001-99980 | 4/2001 |
| JP | 2002228495 | 8/2002 |
| JP | 2003-270004 | 9/2003 |
| WO | WO 2004/025223 A3 | 3/2004 |
| WO | WO 2006/069879 A1 | 7/2006 |

* cited by examiner

*Primary Examiner* — John H Le
(74) *Attorney, Agent, or Firm* — Bacon & Thomas, PLLC

(57) ABSTRACT

A method for monitoring a sensor function by repeatedly acquiring data records including sensor-specific calibration data; by storing the acquired data records; by analyzing changes of the calibration data over time using the stored data records; and by determining time or time weighted with a load factor until the next calibration is due, using at least the changes of the calibration data over time. The resulting time or the determined time weighted with a load factor can, for example, be output in suitable form directly after determination, thereby allowing for a long-term planning of calibration, and/or it can be stored as a date or a remaining time. A comparison with a time signal or a count-down of the remaining time allows at the due date to output a request, or prompt, signal, optionally with a desired lead time.

21 Claims, 4 Drawing Sheets

Absolute Load Equivalents

Relative Load Equivalents

Relative Load Counter

METHOD FOR FUNCTION MONITORING OF A SENSOR

TECHNICAL FIELD

The present invention relates to a method for function monitoring of a sensor, especially a potentiometric sensor.

BACKGROUND DISCUSSION

Simple operation, safety, and reliability are most important requirements for measuring points for monitoring processes, be it for reasons of process optimization or for the monitoring and observance of limit values. Measuring points today supply the operator with measured value information and, in some few cases, additional information about the current condition of the system. In such case, it is monitored e.g. whether limit values are currently exceeded or whether and how sensor-specific parameters, like the glass impedance of a pH sensor, are being met. Monitoring refers, thus, to current events. In so far as a plant malfunction or shutdown causes very high costs in comparison to the price of the sensor, it is very important to exclude malfunctioning of the measuring point as far as possible in advance, in the context of which a correct and assured, measured value has special meaning.

In WO2004/025223, Wittmer et al. disclose a method for monitoring the function of a sensor, in the case of which a prognosis is given for the service life of a sensor remaining until its replacement becomes necessary. This prognosis is made on the basis of the temporal development of sensor parameters, for example periodically collected calibration data.

Independent of the question of the remaining service life, it is however also necessary to qualify the measuring accuracy of the sensor over the entire service life as certainly as possible. In order to obtain this certainty, the operator, today, must, in the case of important processes, conduct this recalibration/readjustment very frequently, even though the sensor system might, in fact, still be working absolutely correctly. Thus, especially time, but also materials, are used unnecessarily.

SUMMARY OF THE INVENTION

It is therefore an object of the present invention to provide a method for function monitoring of a sensor; and, to a sensor with an integrated system for function monitoring.

The object is achieved according to the invention by the method, including the step of:

repeated collecting of data sets having sensor-specific calibration data;

storing the collected data sets having sensor-specific calibration data;

analyzing temporal development of the calibration data based on the stored data sets; and determining, at least based on the temporal development of the calibration data, time, or time weighted with a loading factor, until a next calibration.

The resulting point in time, or time weighted with a loading factor, can be, for example, output immediately after the determining, in suitable form, so that the calibration can be planned on a long-term basis, and/or it can be stored as a date or remaining time. By comparison with a time signal or by countdown of the remaining time, when a new calibration is due, a reminder, or prompt, signal can be output—if needed, with a desired advance notice.

Typical calibration data are, for example, in the case of a potentiometric sensor, especially a pH-sensor, slope and zero point and/or isotherm intersection.

The repeated collecting of data-sets can be done, in the case of startup, for example, of a new sensor, first after at least a predetermined time interval based on experience. Thus, for the individual sensor, at first no calibration data exists for the actual measuring point. The predetermined time interval can be a plant standard, predetermined by the user, or determined on the basis of boundary conditions. To these boundary conditions can belong, besides the desired measuring accuracy, for example, load equivalents depending, for example, on temperature, pH-value, and/or particulate freight entrained in the measured medium.

As soon as possible, following a first time interval, a second data set of the same sensor-specific calibration data is collected, then the change of the calibration data can be referenced for determining the next calibration point in time, or the time period until the next calibration.

For analyzing the temporal development of the calibration data, especially the difference relative to the calibration data of the previous data-set can be computed.

In determining the next point in time for a calibration and/or an adjustment, besides the change of the calibration data, the elapsed time since the preceding calibration, and boundary conditions, such as minimum permissible slope and/or maximum zero-point shift, can be considered.

In the simplest case, determination of the next calibration point in time can be done assuming linear behavior of the sensor. I.e., the temporal development of the calibration data can be linearly extrapolated, and the next calibration point in time set timely before the expected attainment of a critical value. Assuming process conditions remain constant, this forecast becomes ever more exact, as the number of calibration data sets considered in the computation increases. Taking into consideration further sensor characteristics such as total actual working time or load data, a more differentiated algorithm can be used. For example, the elapsed time can be weighted with a load factor, into which the aforementioned load parameters can enter. In this embodiment of the invention, a prompt signal for the calibration is requested, if, for example, the integral of the load over time, or the sum of the load equivalents over time intervals, since the last calibration has achieved a certain load*time value.

To this end, the pH sensor measures, besides the pH value, also a load parameter of significance. Many pH-transducers also have a temperature sensor, so that the parameters for determining the load integral over time are directly available.

Extreme values load sensors more strongly than moderate values. In the example of a pH-sensor, this means that pH values around 0 or 14 load a sensor more than pH value 7. High temperatures likewise load more highly than moderate temperatures, so that, therefore, a combination of extreme pH values and high temperatures load the sensor more than just high temperatures at pH 7 or extreme pH values at room temperature.

The loading of the sensor can be classified in so-called load equivalents, with which, for example, the time period of operation is to be weighted according to the mentioned conditions.

Further parameters are, for example, blocking tendency of the diaphragm of the pH sensor, which is measurable via the diaphragm resistance, abrasion on the pH-sensitive glass, which can be determined via the glass resistance, steepness of the change in pH or change in temperature, as well as the number of sterilizations.

These parameters can additionally enter in the determination of the load, and are captured—if relevant—in a suitable algorithm, which is a counter in the simplest case. The higher the load, the more load equivalents are added. The time interval between two calibrations is shortened thereby compared to operating conditions under smaller load. The higher the value of the load equivalents, the earlier the sensor must be calibrated.

In other words, the invention is based on evaluating a history of the last calibrations on the basis of the corresponding data, and from this, possibly with consideration of changing loads of a sensor, compute a time at which the sensor must be recalibrated/readjusted, in order to maintain the sensor parameters required by the operator.

In this way, unnecessary calibrations of a sensor in a measuring point can be avoided, and the correct measured value is assured at reduced costs.

The potentiometric sensor of the invention, especially for implementation of the method of the invention, includes: A primary sensor and circuit means The potentiometric sensor can further include at least one auxiliary sensor, especially a temperature sensor, for ascertaining a load-relevant variable.

BRIEF DESCRIPTION OF THE DRAWINGS

The invention will now be explained on the basis of an example of an embodiment shown in the drawings, the figures of which show as follows.

DETAILED DISCUSSION

The diagrams in FIGS. 1 to 4 involve data of a pH sensor. Essential characteristics of a pH of sensor are the zero, or null, point NP and the sensitivity E. These characteristics must be calibrated at regular intervals, in order to assure the measuring accuracy of the measuring system.

Figure 1:
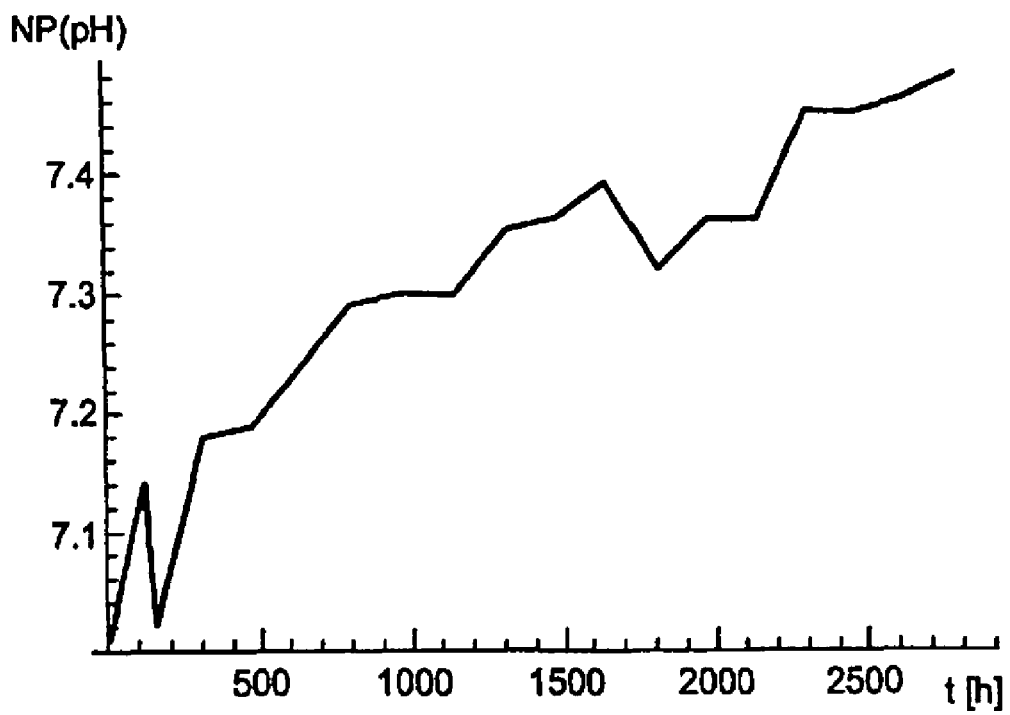
FIG. 1 for a pH sensor, an example of the change of the sensor null, or zero, point NP, in pH, as a function of time t, in hours.
Figure 2:
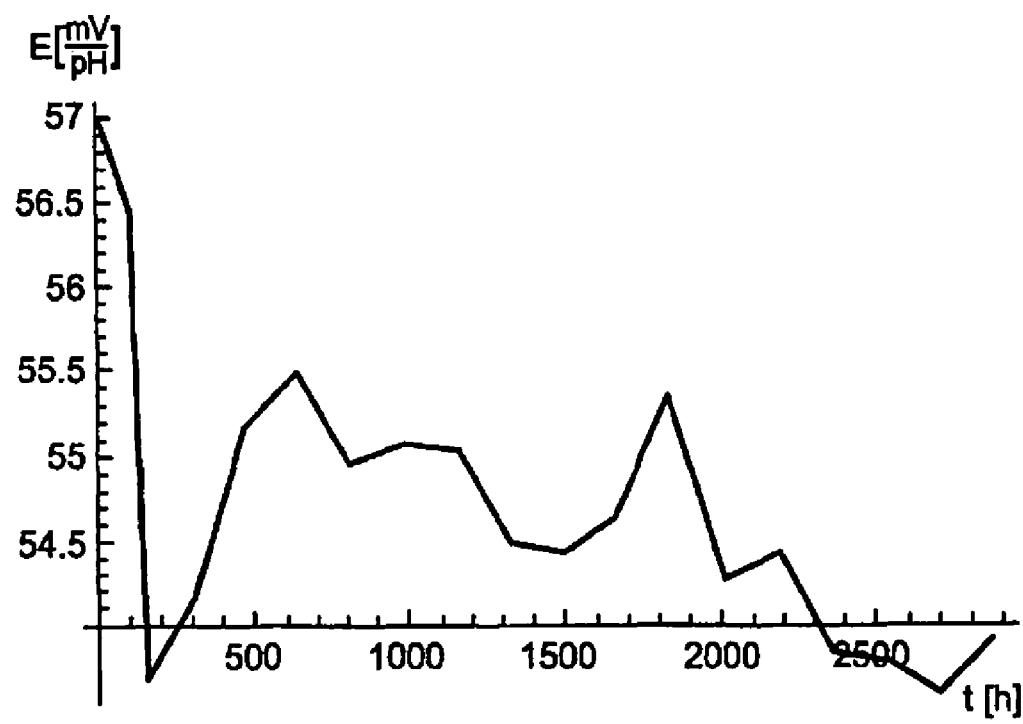
FIG. 2 for a pH sensor, an example of change of sensitivity E, in mV/pH, as a function of time t, in hours.
Figure 3:
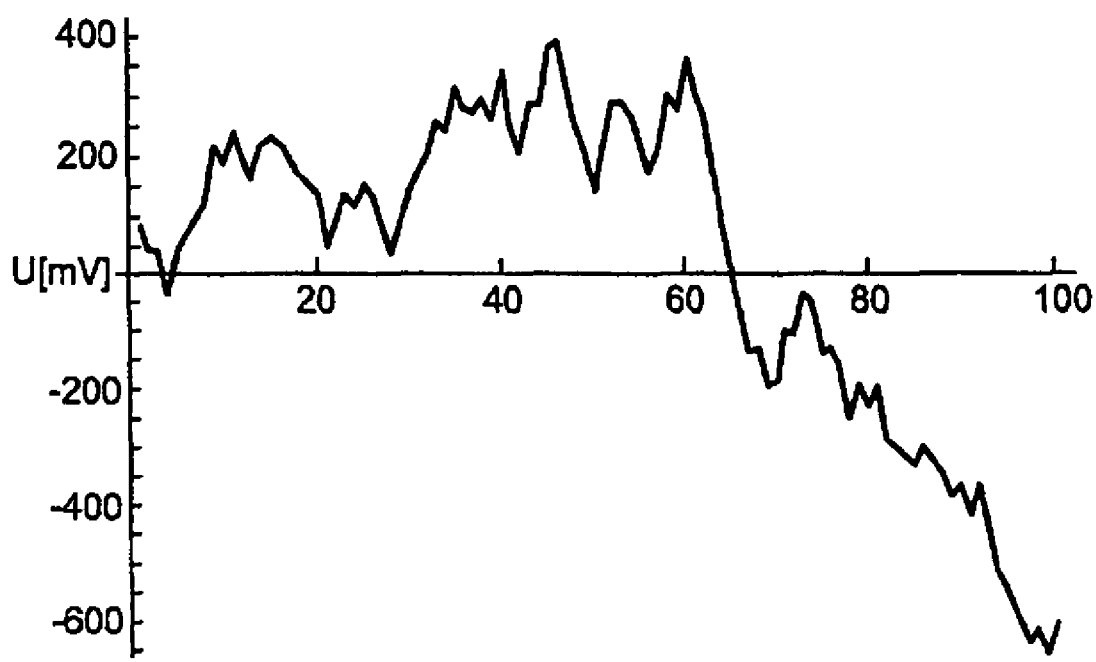
FIG. 3 for a pH sensor, a simulated typical curve for measured-voltage U, in mV, over a time period of 100 hours.
Figure 4:
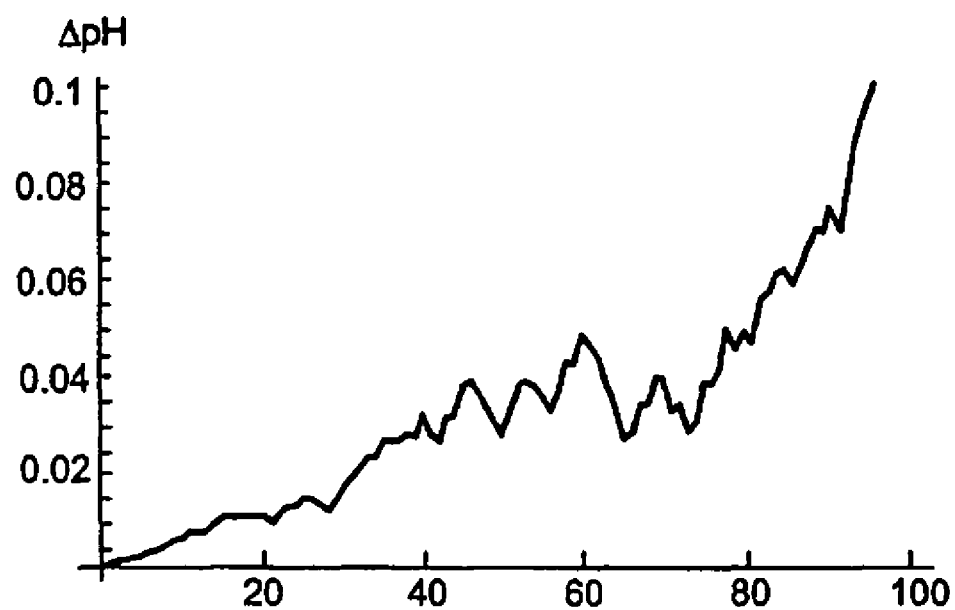
FIG. 4 a plot of estimated pH measurement error $\Delta$pH for the measured voltage curve of FIG. 3, based on the data of FIGS. 1 and 2, as a function of time and measured voltage.

The operating conditions influence the changes of these characteristics. The rate of change of these characteristics reflect, as it were, the operating conditions. FIGS. 1 and 2 show typical data of the temporal development of zero point and sensitivity of a pH sensor as a function of time. Each data point corresponds to a calibration value which, according to the invention, is stored in a data set. Via knowledge of the temporal development in the past, one can infer changes in the future. In the simplest case, this is done through a linear smoothing function AE(t) for the sensitivity and ANP(t) for the zero point.

FIGS. 1 and 2 show the behavior of sensor data over 2820 hours. An approximate regularity of the development of zero point and sensitivity for a certain type of sensor is the prerequisite for a prognosis for the development of sensor parameters since the last calibration. On this basis, the next calibration point in time can be ascertained. The time spans in question can vary, depending on sensor type and load, for example between about 10 hours and several days.

From the historical data for the null point NP and sensitivity E, AE(t) and ANP(t) can be derived. With these, a hypothesis can be established concerning the temporal changing of E and NP. During pH measurement in the 100 h since the calibration following 2820 operating hours, shown in FIG. 3 as a simulated measured voltage curve of a pH sensor as a function of time, the pH value pHMEAS is ascertained, however, from the calibration data of the point in time t=2820 h.

On the basis of the measured voltage and the hypothesized characteristic data EHYP and NPHYP for a point in time >2820 h, a hypothetical pH measured value pHHYP can be calculated. The difference between pHHYP and pHMESS can be considered the pH measurement error. This is displayed in FIG. 4 for the 100 h following 2820 h.

A user can input to the measurement transmitter the error which he or she is willing to accept. Upon reaching this value, a prompt for calibration is generated. When, as here in the example, a maximum absolute pH error of 0.06 pH was specified, the prompt would be generated following about 85 h.

The present method can also be implemented on the basis of relative error.

The method as described here has to this point been executed without taking load equivalents into consideration. This is justified in the case of loading conditions remaining the same.

In the case of fluctuating loading, consideration of load equivalents, e.g. a weighting of operating time with load equivalents, is advantageous. Typical values of load equivalents for a particular pH sensor are given in Table I:

TABLE I

| | T[° C.] | | | | | |
|---|---|---|---|---|---|---|
| pH | −20...20 | 20...40 | 40...60 | 60...80 | 80...100 | 100...120 |
| 14 ≥ pH > 12 | 4 | 8 | 12 | 16 | 20 | 24 |
| 12 ≥ pH > 10 | 3 | 6 | 9 | 12 | 15 | 18 |
| 10 ≥ pH > 8 | 2 | 4 | 6 | 8 | 10 | 12 |
| 8 ≥ pH > 6 | 1 | 2 | 3 | 4 | 5 | 6 |
| 6 ≥ pH > 4 | 2 | 4 | 6 | 8 | 10 | 12 |
| 4 ≥ pH > 2 | 3 | 6 | 9 | 12 | 15 | 18 |
| 2 ≥ pH > 0 | 4 | 8 | 12 | 16 | 20 | 24 |

This principle can be implemented simply with a load counter, in the case of which the current load equivalent per unit of time is added to the load balance. The prognosis for service time until the next calibration is, accordingly, a prognosis by way of the load equivalents until the next calibration.

When, for example, the sensor of the above example was subjected in the time period before the last calibration at 2820 hours to an average load equivalent LE=4, and, per minute, the current load equivalent is added, then, in the above example, a prognosis for a load service time of 85*60*4=20400 load equivalent minutes would have been given, instead of the 85 hours.

In the case of an increase of the average load to a load equivalent of 8 following the calibration leads to the 20400 load equivalent minutes being already used up after 42.5 hours.

A monitoring system associated with the sensor and adding the load equivalents up would, accordingly, prompt for a calibration already after 42.5 hours, or a total operating time of 2862.5 hours. In the case of a lesser loading, the time would, in contrast, be weighted with a lesser factor, so that, for example in the case of a loading factor of 1, the next calibration would be prompted first after 340 hours.

In a further development of this point of view of the invention, the influence of the loading factor on the prognosis of the time until the next calibration can be weighted, for example, in order to take safety aspects into consideration. Thus, perhaps an increase of the loading compared to a time period before the last calibration, on whose basis the prognosis for the current time period was established, can be fully added on, while a decrease of the loading, which leads to a lengthening of the service time until the next calibration, can be taken into consideration using a lesser weight, in order to prevent an overly long extension of the service time between two calibrations from one time period to the next. For this, a simple summing of the load equivalents is not sufficient, for this procedure does not lead to a recognition of whether the loading has increased or decreased. Instead, the current load is, in fact, still added in a first counter, in order to ascertain an actual average loading following expiration of the service time. The prognosis for the service time is now given in loading time units, which are normalized with the average loading of the just preceding calibration interval. To the 20400 loading equivalent minutes at an average loading equivalent of 4 thus correspond 5100 minutes.

For ascertaining the end of the current service time, the current loading in each time unit is divided by the average loading equivalent of the preceding calibration time period and then balanced in a second counter. When the quotient amounts to at least 1, it is added unchanged, otherwise the square root of the quotient is added. Upon reaching the prognosis value, here 5100 normalized minutes, a new calibration is prompted. The introduction of the root function for ascertaining the weighting factor in the case of decreasing loadings means that the calibration time periods can be lengthened more slowly than shortened. This leads, it is true, to an increase of the calibration effort compared with a solution without this factor, but such serves the goal of safety.

In this way, a lessening of the average loading in the current calibration time period by a factor of 4 leads only to a doubling of the length of the calibration time period and not to a quadrupling.

Figure 5A:
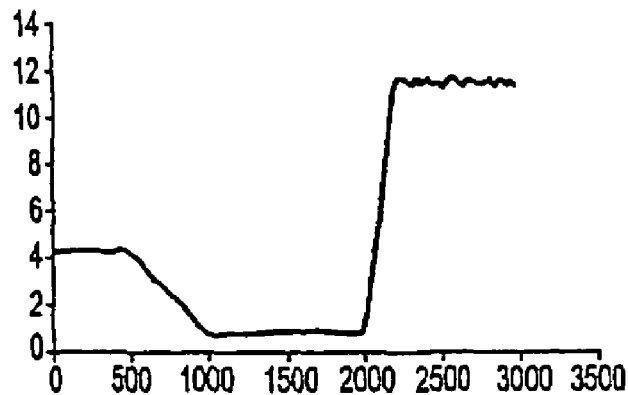
FIG. 5 an example of a weighting of service life with load equivalents.
Figure 5B:
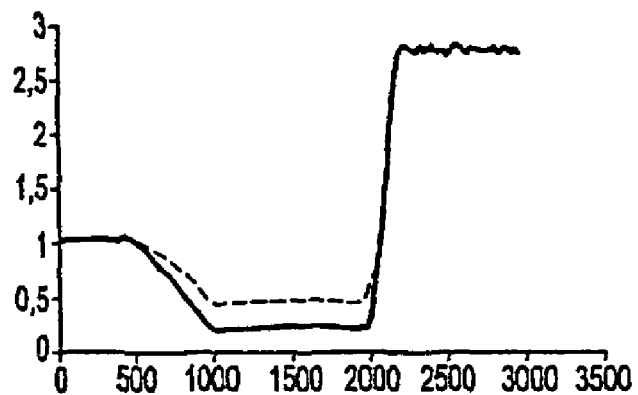
Figure 5C:
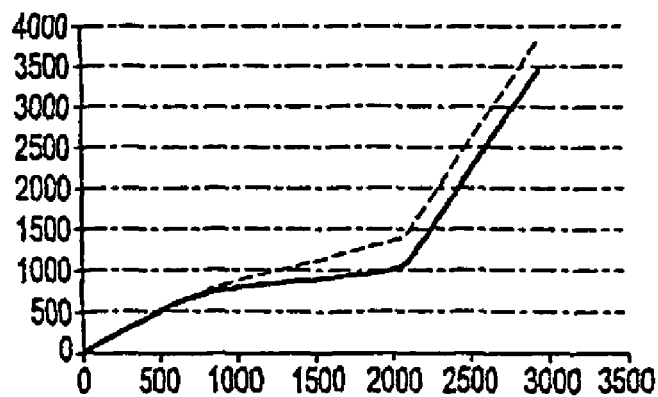

FIGS. 5 *a* to *c* illustrate this aspect of the invention again in context. FIG. 5*a* shows the temporal development of the absolute loading equivalent on a sensor during the time since the last calibration. The average loading equivalent in the time interval before the last calibration amounted to 4.2. The curve of the normalized loading in the current interval is plotted in FIG. 5*b*. The solid curve shows the usual normalization by simple division. The dashed line shows the normalization "with factor of safety", according to which in the case of quotients below 1 their square root is counted as relative loading. The resulting sum of the counter level for the relative loadings is shown for the two different weightings is shown in FIG. 5 *c*. The solid line is for usual normalizing and the dashed line for the normalizing with factor of safety.

The effects on the calibration time period are as follows.

If, for example, a time period of 1000 minutes would have been predicted in the case of loading remaining the same at 4.2 loading equivalents, then the simple normalizing would, due to the lowered loading, effect a service time of 2020 minutes until the next prompt for calibration. Normalizing with factor of safety effects, in contrast, a lesser lengthening of the service time; the calibration prompt is issued already after 1300 minutes.

A possibly too early calibration prompt in the case of sinking loading is corrected by, in the next calibration, the actual change of the calibration data being taken into consideration, and, in this way, the next interval, in the case of lessened changes of the calibration data, is again made longer.

Figure 6:
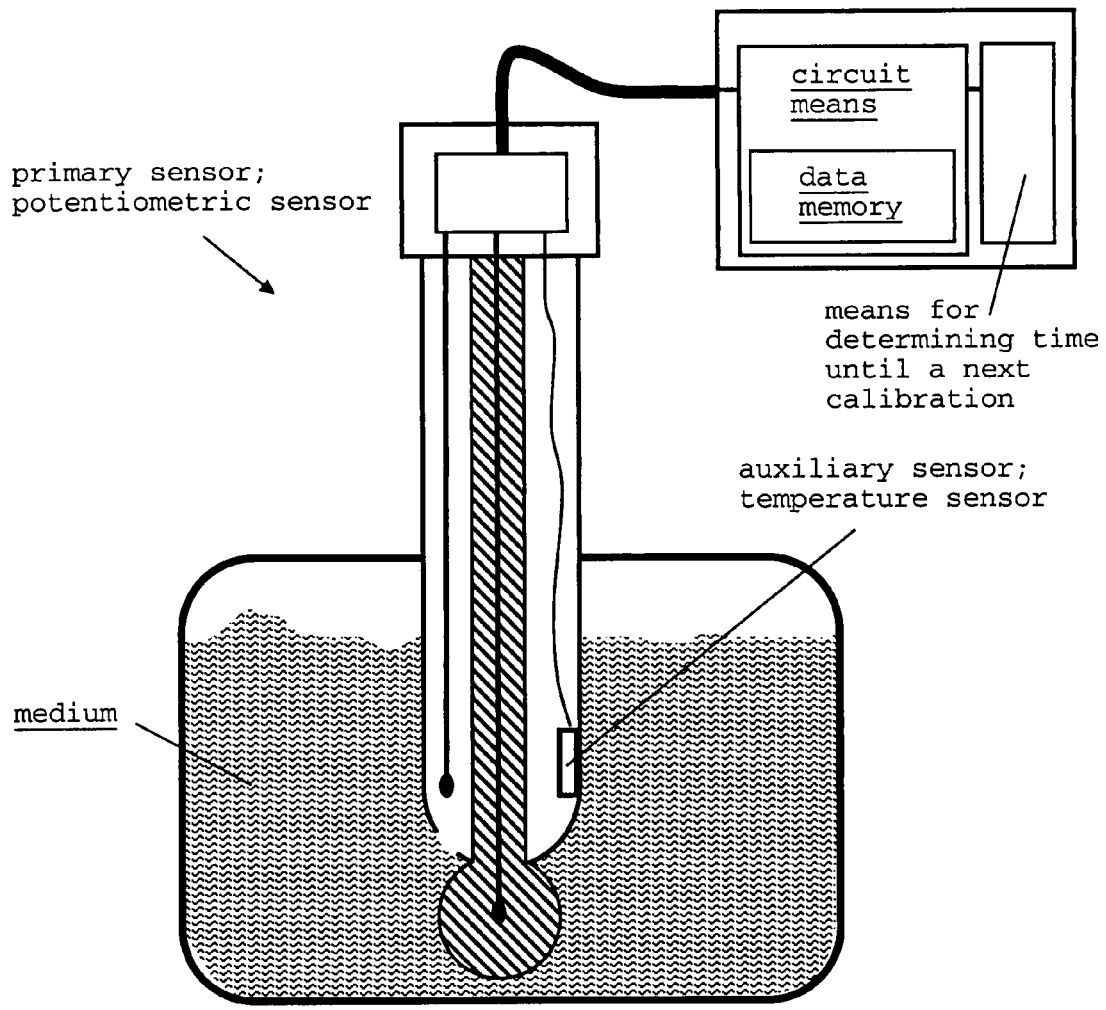
FIG. 6 schematically illustrates a potentiometric sensor according to the invention.

A special potentiometric sensor is a glass electrode as shown in FIG. 6 for example.

The potentiometric sensor of the invention, especially for implementation of the method of one of the preceding claims, includes: A primary sensor for registering a potentiometric, measured variable, and for outputting a measured-variable-dependent, primary signal; circuit means for processing the primary signal or a signal derived therefrom, wherein the circuit means includes a data memory for current calibration data and calibration data of at least one previous calibration; and means for determining, on the basis of the temporal development of the calibration data, the length of time until the next calibration. The potentiometric sensor can further include at least one auxiliary sensor, especially a temperature sensor, for ascertaining a load-relevant variable.

The invention claimed is:

1. A method for function monitoring of a potentiometric sensor, comprising the steps of:
repeatedly acquiring of data sets having sensor-specific calibration data wherein the calibration data is at least one of slope or zero point or isothermal intersection point;
storing the collected data sets having sensor-specific calibration data;
analyzing temporal development of the calibration data based on the stored data sets; and
determining, at least based on the temporal development of the calibration data, time, or time weighted with a loading factor, until a next calibration, wherein:
the temporal development of the calibration data is linearly extrapolated, and the next calibration is set timely before the expected attainment of a critical value of the calibration data.

2. The method as claimed in claim 1, wherein:
the resulting point in time or the time weighted with a loading factor is output immediately after determination.

3. The method as claimed in claim 1, wherein:
the time or time weighted with a loading factor is stored as remaining time and serves as a comparison for a counter which counts operating time.

4. The method as claimed in claim 3, wherein:
the counter weights the operating time with current loading equivalents.

5. The method as claimed in claim 1, wherein:
the potentiometric sensor is a pH sensor.

6. The method as claimed in claim 1, wherein:
said repeatedly acquiring of data sets is done in the case of startup of a new sensor first after at least a predetermined time interval, and the resulting current data set of the sensor-specific calibration data is referenced for ascertaining temporal development of the calibration data and a next calibration point in time.

7. The method as claimed in claim 1, wherein:
in determining the time or time weighted with a loading factor until a next calibration, minimum allowable slope, or maximum zero, point shift are taken into consideration, in addition to change of the calibration data.

8. The method as claimed in claim 1, wherein the time until the next calibration is weighted or normalized with loading equivalents or parameters derived therefrom.

9. The method as claimed in claim 1, wherein loading equivalents depend on one or more of the following variables: temperature, pH value, sensor abrasion, slope of pH-change or temperature change, number of sensor sterilizations.

10. A potentiometric sensor, comprising:
a primary sensor for registering a potentiometric, measured variable and for issuing a measured-variable-dependent, primary signal; and
circuit means for processing the primary signal or a signal derived therefrom wherein:
said circuit means includes a data memory for current calibration data and calibration data of at least one earlier calibration, said calibration data being at least one of slope or zero point or isothermal intersection point;
means for determining, based on temporal development of the calibration data, time until a next calibration, the temporal development of the calibration data is linearly extrapolated, and the next calibration is set timely before the expected attainment of a critical value of the calibration data
the time until the next calibration is weighted or normalized with loading equivalents or parameters derived therefrom; and
said loading equivalents depend on one or more of the following loading-relevant variables; temperature, pH value, sensor abrasion, slope of pH-change or temperature change, number of sensor sterilizations.

11. The potentiometric sensor as claimed in claim 10, further comprising:
at least one auxiliary sensor for registering a loading-relevant variable.

12. The potentiometric sensor as claimed in claim 11, wherein:
said auxiliary sensor is a temperature sensor.

13. A method for function monitoring of a potentiometric sensor, comprising the steps of:
repeatedly acquiring of data sets of sensor-specific calibration data;
storing said data sets of sensor-specific calibration data;
analyzing temporal development of the calibration data based on said stored data sets; and
determining, at least based on the analysis of the temporal development of the calibration data, time until a next calibration, the time until the next calibration being weighted or normalized with loading equivalents or parameters derived therefrom, wherein:
said loading equivalents depend on one or more of the following variables: temperature, pH value, sensor abrasion, slope of pH-change or temperature change, number of sensor sterilizations.

14. The method as claimed in claim 13, wherein:
the time weighted with a loading factor is stored as remaining time and serves as a comparison for a counter which counts operating time.

15. The method as claimed in claim 14, wherein:
the counter weights the operating time with current loading equivalents.

16. The method as claimed in claim 13, wherein:
the calibration data comprises slope and zero point or isothermal intersection point.

17. The method as claimed in claim 13, wherein:
the potentiometric sensor is a pH-sensor.

18. The method as claimed in claim 13, wherein:
said repeatedly acquiring of data sets is done in the case of startup of a new sensor first after at least a predetermined time interval, and the resulting current data set of the sensor-specific calibration data is referenced for ascertaining temporal development of the calibration data and a next calibration point in time.

19. The method as claimed in claim 13, further comprising the step of:
forming a difference with respect to the calibration data of a preceding data set for analyzing temporal development of the calibration data.

20. The method as claimed in claim 13, wherein:
in determining the time until the next calibration, minimum allowable slope, or maximum zero point shift are taken into consideration, in addition to change of the calibration data.

21. The method as claimed in claim 13, wherein:
determining of the time until the next calibration is done based on a linear extrapolation of change of calibration data as a function of time.

* * * * *